(12) United States Patent
Mikhaeil

(10) Patent No.: US 9,886,555 B2
(45) Date of Patent: Feb. 6, 2018

(54) METHOD AND APPARATUS FOR DISPENSING MEDICAMENTS

(71) Applicant: Sami G. Y. Mikhaeil, Mississauga (CA)

(72) Inventor: Sami G. Y. Mikhaeil, Mississauga (CA)

( * ) Notice: Subject to any disclaimer, the term of this patent is extended or adjusted under 35 U.S.C. 154(b) by 0 days.

(21) Appl. No.: 15/387,747

(22) Filed: Dec. 22, 2016

(65) Prior Publication Data

US 2017/0169188 A1    Jun. 15, 2017

Related U.S. Application Data

(62) Division of application No. 13/277,295, filed on Oct. 20, 2011, now Pat. No. 9,563,925.

(30) Foreign Application Priority Data

Oct. 21, 2010 (CA) ...................... 2718278

(51) Int. Cl.
| | |
|---|---|
| *G06F 19/00* | (2011.01) |
| *A61J 7/00* | (2006.01) |
| *A61J 7/02* | (2006.01) |
| *A61J 7/04* | (2006.01) |
| *G06Q 10/04* | (2012.01) |
| *G06Q 50/24* | (2012.01) |

(52) U.S. Cl.
CPC ........ *G06F 19/3462* (2013.01); *A61J 7/0076* (2013.01); *A61J 7/02* (2013.01); *A61J 7/049* (2015.05); *A61J 7/0436* (2015.05); *A61J 7/0445* (2015.05); *A61J 7/0463* (2015.05); *G06Q 10/047* (2013.01); *G06Q 50/24* (2013.01)

(58) Field of Classification Search
CPC ............... G06F 19/3462; G06F 19/326; G06F 19/3406; G06F 19/3456
USPC .......... 141/1, 83, 94, 98; 700/240, 241, 244, 700/236, 265
See application file for complete search history.

(56) References Cited

U.S. PATENT DOCUMENTS

| | | | |
|---|---|---|---|
| 5,597,995 A | 1/1997 | Williams et al. | |
| 6,202,923 B1 * | 3/2001 | Boyer | ................. G06F 19/3462 235/375 |
| 7,028,723 B1 | 4/2006 | Alouani et al. | |
| 2006/0041330 A1 | 2/2006 | Ansari et al. | |

\* cited by examiner

*Primary Examiner* — Timothy L Maust
*Assistant Examiner* — Timothy P Kelly
(74) *Attorney, Agent, or Firm* — Manelli Selter PLLC; Edward J. Stemberger

(57) ABSTRACT

A pharmacy workflow platform and prescription checking and medicament dispensing station and method comprising (a) script display means; (b) scanning means for providing script data and stock bottle label data in electronic format from the prescription and a stock bottle label; (c) CPU means comprising i) means for receiving and storing the script data and stock bottle data in electronic format; ii) means for transferring the script data to the script display means to effect display of the script; iii) means cooperable with medicament dispensing weighing and counting means; (d) medicament-dispensing weighing means in communication with the CPU means; and (e) control means for controlling the CPU means. Medication is dispensed in a more safe, efficient and cost-effective manner.

10 Claims, 3 Drawing Sheets

METHOD AND APPARATUS FOR DISPENSING MEDICAMENTS

This Application is a Division of application Ser. No. 13/277,295 filed on Oct. 20, 2011, which claims priority from Canadian Patent Application No. 2,718,278, filed on Oct. 21, 2010.

FIELD OF THE INVENTION

This invention relates to a method and apparatus for dispensing medicaments, and more particularly to a pharmacy workflow platform, a prescription checking and medicament dispensing station, a network thereof, and methods therewith.

BACKGROUND OF THE INVENTION

There is an increasing need to dispense medicaments to individuals in pharmacies, hospitals, health centres and the like, in a safe, efficient and cost effective manner. Currently, medication errors can result from confusion over "look-alike" or "sound-alike" product names. If patients receive an incorrect drug or dosage, these errors can result in serious harm to the patient. One common cause of confusion is from a name mix-up, caused by what human factors experts call "confirmation bias", where a practitioner reads a poorly written drug name and is most likely to see in that name that which is most familiar to him;—overlooking any discontinuing evidence.

The modern pharmacy practice therefore requires equipment and record keeping capabilities in order to enhance the safe and accurate dispensing of prescriptions. However, recently, there is the desire to also provide pharmacy services to the public, without a pharmacist being physically present. This is a process that creates the need to provide a safe and efficient communication tool for the pharmacist, in order that he/she can remotely supervise the prescription filling procedures.

SUMMARY OF THE INVENTION

The advantages set out hereinabove, as well as other objects and goals inherent thereto, are at least partially or fully provided by the pharmacy workflow platform, and prescription checking and medicament dispensing station of the present invention, as set out herein below.

Accordingly, it is a principal advantage of the present invention to provide a prescription cheek point and medicament dispensing work station which provides for enhanced safety, efficiency, and convenience with single on-site, off-site, and/or network operations, i.e. systems having remote locations for the dispensation of medicaments.

This is achieved by superior processes for the validation of information and data, as prescribed by an authorized medical professional, and improved detection of mismatches to reduce errors in such dispensation. Such information relates to patient information in order to ensure the selection of the proper patient intended for the prescribed medication, such as, for example, name, possible alternate name, address, date of birth, telephone number, prescription information, including the prescriber's name, address, telephone, license number, and drug information such as DIN number, brand name, generic name, strength, amount, dosage, form, pack size and the like.

Verification and confirmation of the used stock bottle and proper medication as prescribed through verifying DIN/NDC number against prescription data, is also desired, and is provided by displaying a unit image which can be compared with the selected product, and systems to ensure the proper quantity of pills are counted, and placed directly into the patient's prescription drug vial, to avoid cross contamination.

Further, in case of short stock quantity, the system also preferably keeps a record of the owing balance quantity.

In preferred embodiments, the pharmacy workflow platform, and the prescription checking and medicament dispensing station, and method, provides for:

- the scanning and capture of the prescription "script", whereby the system prompts the operator to scan the original script while interfacing with the dispensing software and displays the information as entered;
- Interfacing with dispensing system to retrieve information as entered and matches against the original script;
- Providing for two or more authorization levels, e.g. the pharmacist and an authorized technician to override mismatched information;
- Identifying the selected stock bottle before filling. Preferably, this is confirmed by verification of the prescription drug DIN number or NDC code, against the prescription in to validate the correct stock bottle has been used, and/or that the proper drug is dispensed;
- automatic CPU control of the drug counting step which alerts the operator if the counted pills are not properly equal to the desired dispensed quantity. Preferably, this is achieved by counting pills directly in vials, so that they are dispensed without any cross contamination with other medication;
- Keeping track of owing balance if the counted pills are less than prescription quantity;
- Capturing image(s) of the dispensed vial with the pills inside;
- Remotely monitoring filling procedures via live video communication; and
- Allowing audio/video communication between personnel;—particularly between the pharmacist and the technician.

Accordingly, the invention in one aspect provides a prescription checking and medicament dispensing station comprising:

(a) script display means;
(b) scanning means for providing script data and stock bottle label data in electronic format from said prescription and a stock bottle label;
(c) CPU means comprising:
  i) means for receiving and storing said script data and stock bottle data in electronic format;
  ii) means for transferring said script data to said script display means to effect display of said script; and
  iii) means cooperable with medicament dispensing weighing means;
(d) medicament-dispensing weighing means in communication with said CPU means; and
(e) control means for controlling said CPU means.

Preferably, the station additionally has label printing means for providing printed vial label in communication with the CPU means as hereinabove defined.

Preferably, the station also comprises medicament counting means in communication with the CPU means.

The invention in one embodiment provides a station as hereinabove defined wherein the control means is selected from means comprising keyboard means, touch screen computer means, bar code receiving means and machine readable code means.

The invention in further embodiments provides a station as hereinabove defined wherein the scanning means comprises a bar code scanner.

In further embodiments a station as hereinabove defined further comprises photographic means selected from a camera and web-cam.

Preferably, the station further comprises printing means.

The invention in further embodiments provides a station as hereinabove defined constituted as an "on-site" station comprising a bench, table, kiosk or the like.

The invention in further embodiments provides a station as hereinabove defined Wherein the CPU means comprises stored data and means to effect comparison of the script data and the stock bottle label data with the stored data to detect and identify any mistakes.

In a further aspect, the invention provides a prescription checking and medicament dispensing network comprising one or more stations as hereinabove defined in communication with an "off-site" centre.

In further embodiments, the invention provides a network as hereinabove defined wherein the "off-site" centre is adapted to:
 i) receive said script data and stock bottle label data in electronic format;
 ii) receive said prescription and said printed vial label by said photographic means; and
 iii) monitor said medicament dispensation, In a further aspect, the invention provides a desired primary source information network comprising a plurality of on-site apparatus as hereinabove defined; and a central control and data storage means cooperable with each of said apparatus to provide said desired primary source information from said apparatus to said central control.

In a yet further aspect, the invention provides a method for dispensing a medicament prescribed on a prescription from a medicament containing stock bottle having a label,
 said method comprising
 (a) scanning said prescription and said label to provide script data and said label data in electronic format;
 (b) providing display means;
 (c) providing CPU means comprising
  i) means for storing said script data and said label data in electronic format;
  ii) means for transferring said script data to said display means;
 (d) controlling said CPU means under controller means;
 (e) displaying said script data on said display means to provided displayed script data;
 (f) visually comprising said entered prescription data with said displayed script data to detect and identify any script's entry mistakes;
 (g) providing acceptable script data;
 (h) providing medicament-weighing and counting means in communication with said CPU means; and
 (i) enabling the storing and reporting of the information required in a transaction describing the dispensing of a drug.

Preferably, the method as hereinabove defined further comprises a system for providing vial label printing means; and, for printing said acceptable script data and said label data on a vial label to provide a printed vial label dispensing a selected amount of said medicament in a vial under the control of said CPU means.

In a yet further aspect, the invention provides a method for providing a person with desired primary source medical information in visual format, said method comprising
 (i) providing CPU means; and
 (ii) feeding primary source information comprising secondary and tertiary data to said CPU means;
 said CPU means comprising means to effect a comparison of said primary source information with said secondary data and said tertiary data to detect and identify any one or more mismatches between said primary source information and said secondary and tertiary data;
 (iii) effecting said comparison to provide any mismatch; and
 (iv) visually displaying said primary source information subjected to said comparison as said desired primary source information.

In further embodiments, the invention provides a method as hereinabove defined wherein said CPU means comprises stored data and means to effect comparison of said primary source information with said stored data to detect and identify any mismatches between said primary source information and said stored data.

In further embodiments, the invention provides a method as hereinabove defined wherein:
 said primary source information comprises "dispensed information";
 said secondary data is store shelf data; and
 said tertiary data comprises Rx script data.

In further embodiments, the invention provides a method as hereinabove defined comprising displaying said visual data on a visual display means.

In further embodiments, the invention provides a method as hereinabove defined comprising displaying said desired primary information remotely offsite from said CPU means.

CPU means is preferably a computer, server, or the like, or any other suitable computing device.

In further embodiments, the invention provides a method as hereinabove defined, wherein said method provides a step by step workflow process, which allows for the distribution of jobs and tasks between pharmacy technicians, and therefore permits the pharmacist to focus on direct patient care. The breakdown of jobs and tasks, and the movement from one step to the next in the process, can be assigned to technicians (or clerks) according to their authority levels. As such, the tasks can be organized according to job responsibilities.

The system of the present invention is also preferably designed to be able to locate any prescription at any time, and thereby, determine the current location and status of the selected prescription, currently in progress.

BRIEF DESCRIPTION OF THE DRAWING

In order that the invention may be better understood, a preferred embodiment will now be described, by way of example only, with reference to the accompanying drawing wherein.

DETAILED DESCRIPTION OF THE PREFERRED EMBODIMENTS

Figure 1:
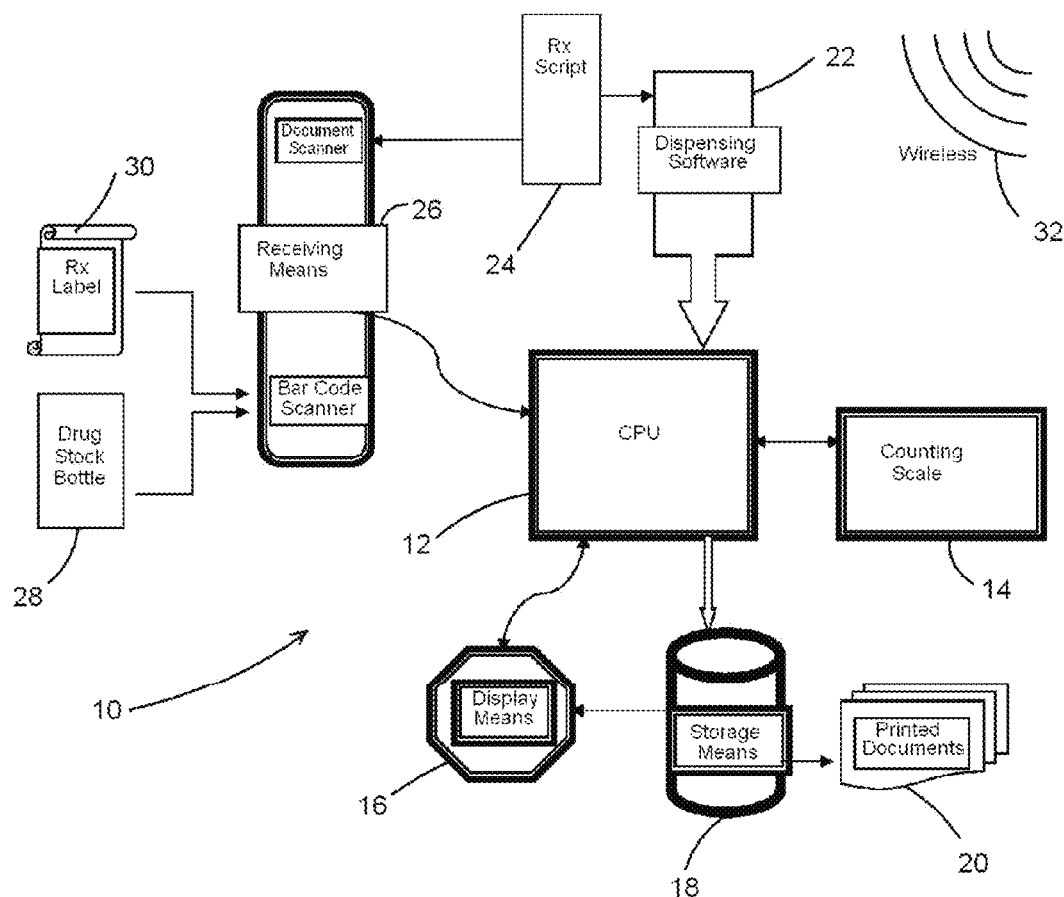
FIG. 1 is a diagrammatic flow chart and prescription checking and medicament dispensing station according to the invention.

The novel features which are believed to be characteristic of the present invention; as to its structure, organization, use and method of operation, together with further objectives and advantages thereof; will be better understood from the following drawings in which a presently preferred embodiment of the invention will now be illustrated by way of example only. In the drawings, like reference numerals depict like elements.

It is expressly understood, however, that the drawings are for the purpose of illustration and description only and are not intended as a definition of the limits of the invention. Also, unless otherwise specifically noted, all of the features described herein may be combined with any of the above aspects, in any combination.

Referring to FIG. 1, this shows generally a prescription checking and medicament dispensing station, generally depicted as station 10, having a CPU 12 which is in communication with counting scale 14, display means 16, data storage file 18, linked to printer 20, dispensing software 22, linked to Rx script 24 and receiving means 26. Receiver means 26 receives drug stock bottle information 28 and. Rx label information 30. CPU is capable of connection to remote stations using a hardwired, or wireless connection 32.

Figure 2:
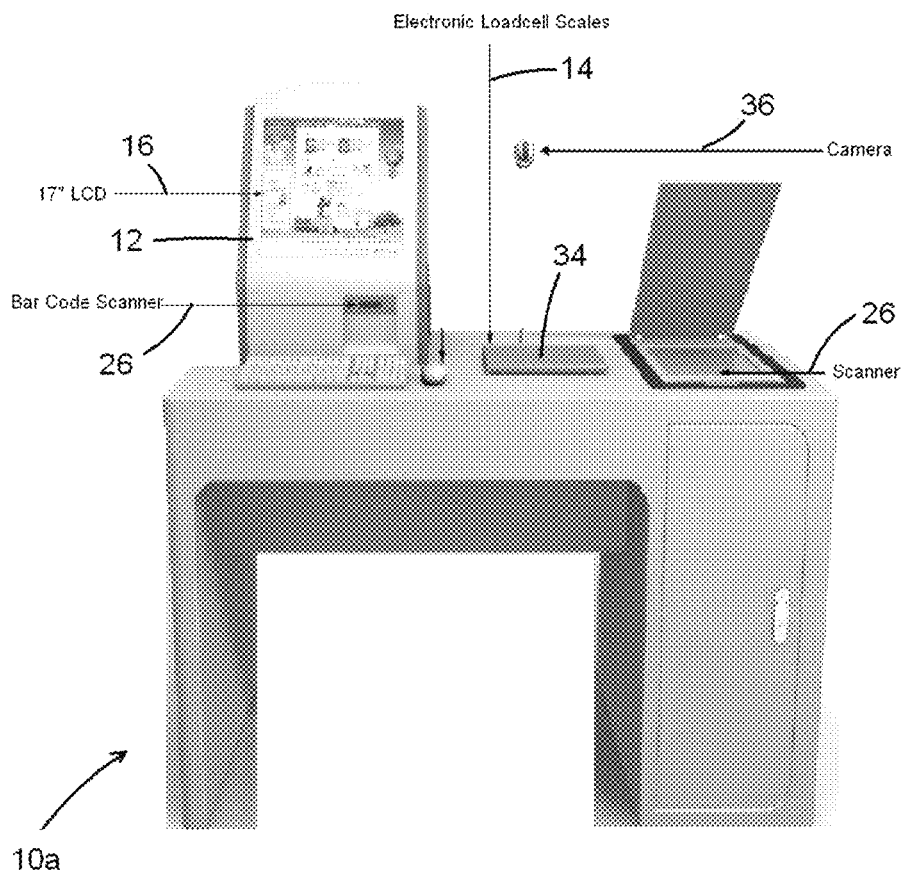
FIG. 2 is a photographic representation of a dispensing station according to the invention.

FIG. 2 shows a representation of one suitable workstation 10a, which includes a number of the features described in FIG. 1.

Figure 3:
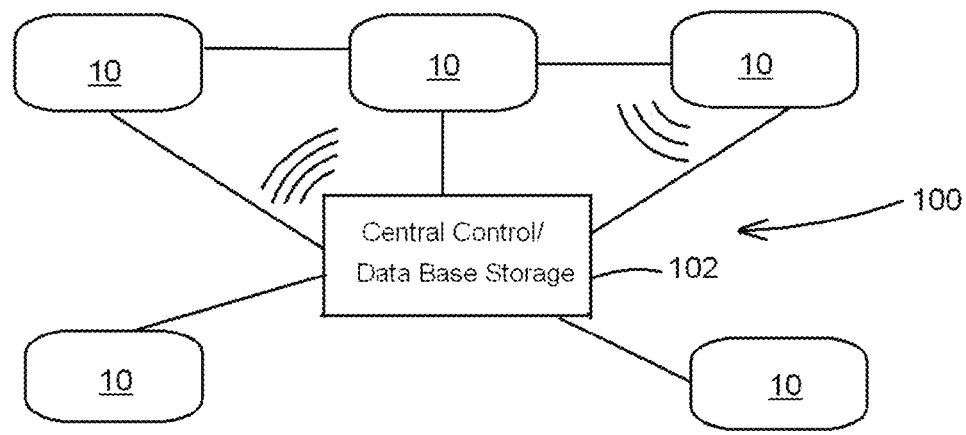
FIG. 3 represents a network of associated dispensing stations according to the invention.

FIG. 3 shows a plurality of stations 10 constituting a network 100 linked to one another, either directly or through a central control unit 102. This connection can be by any suitable means, and can include hardwire or wireless connections.

Figure 4:
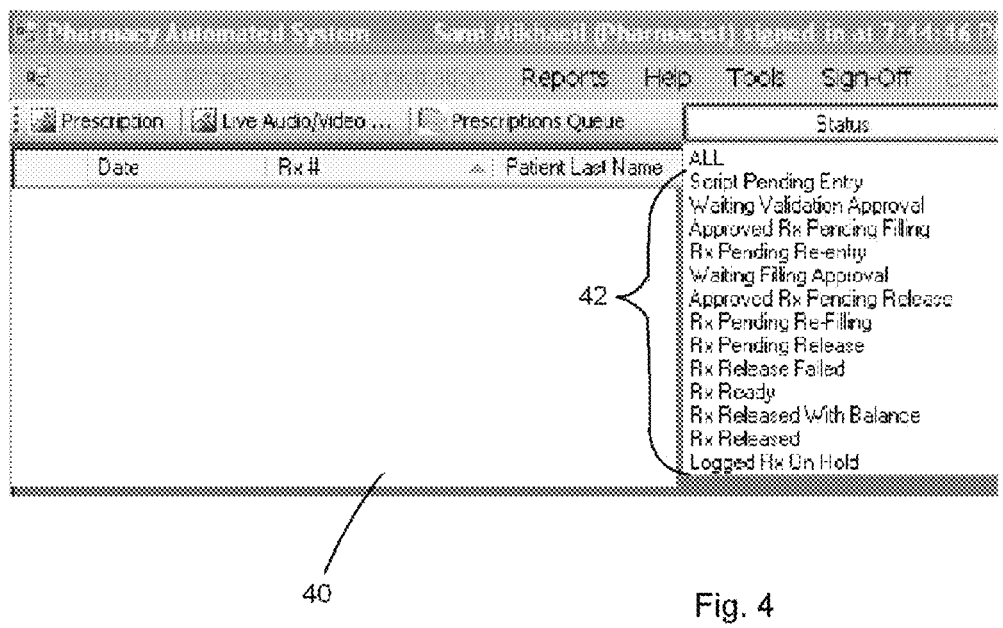
FIG. 4 is a screen shot of one possible computer system, operating in accordance with the present invention.

FIG. 4 shows a computer display 40 that in shows a typical arrangement of choices 42 for an operator of the system.

The process steps are outlined as follows to provide a basic understanding of one embodiment according to the invention.

1. Prescription script 24 originally as written or as orally communicated by a medical prescriber is scanned into receiving means 26. Alternatively, fax and e-prescription documents, can be received directly into CPU 12. This information is uploaded and the resultant script electronic data is stored in storage file 18 under status Script Fending Entry.
2. When convenient, the operator; being either the pharmacist or an authorized technician, recalls the script pending entry information to be displayed on display means 16, and the contents of such script will be entered into dispensing software 22. As a result, a Rx label 30 will be generated.
3. Rx label 30 preferably includes a bar code. The bar code from the label, which has been printed as a result of entering prescription information 24 into dispensing software 22, is scanned to enable interfacing with the dispensing software and to pull the prescription information, as entered, to be viewed on display screen 16.
4. Script information is scanned into CPU 12;—preferably including the patients name, date of birth, Doctor's name, drug name, dosage, amount of drug, and the like.
5. CPU 12 accesses database software 22 to enable script data 24 to be viewed on display screen 16. Entered Prescription Pending Validation is the new status of such prescription in queue.
6. A manual comparison is made between prescription information as entered in the dispensing system and original script 24 as written by the prescriber in order to detect any mismatches. E-prescription is verified automatically by software 22. The operator optionally effects any changes if required.
7. Electronic script data is preferably transmitted and displayed "off-site", through a network, including the global network, by hardwired, or wireless connections 32, for visual comparison and verification of script by the pharmacist, who has the option of adding any reasons for any mismatch, to allow the filling processes to continue. Validated Prescription Pending Filling is now the new status of such prescription in queue
8. Stock bottle label 28 bar code is scanned into CPU 12 which validates stock drug information and matches this information to the information of the prescribed drug using, for example, the drug DIN/NDC number and description, including a pill photo.
9. CPU 12 is manually controlled by keyboard 34.
10. CPU 12 instructs and controls pill counting scale 14 which alerts the operator to dispense the exact quantity of pills into a vial. Vial size is preferably suggested through stored data to facilitate proper vial selection, Software 22 creates owing balance record if necessary.
11. A printed vial label (not shown), part of Rx label, is created from dispensing software 22 and is affixed to vial.
12. The filling procedures, involving an image of the filled vial, its contents and its label, are preferably record using, for example, a web-cam 36 in order to enable live supervision. The resultant display, is optionally sent off-site and is also stored in CPU 12, Filled Prescription Pending Release is the new status of such prescription in queue.

It will be noted that the script electronic data may be (i) sent off-site; (ii) compared with a secondary database to detect mismatched information; and (iii) through software go directly to the pill counter and the final label.

Rx script is scanned to be available in electronic format via step I above by document scanner as part of receiving means 26. This information is uploaded directly to the system in electronic format and the prescription script stored electronically in storage means 18 and is also available for review by an authorized operator.

Rx Label 30 has a bar code and is scanned by a bar code reader which is also part of receiving means 26 in step (3) to initiate a communication between CPU 12 and dispensing software 22 suitable, herein termed "Check Point" software. This software interfaces with the prescription system, pulls the information as entered for this particular prescription and displays such information on display screen 16 along with the electronic copy of the script. The operator, who may be a pharmacist or technician, validates each and every component of the entered information against the original script as written according to the operator's authority level. Mismatched information can be accepted to continue the process of filling the prescription with valid reasons. By scanning the selected pack or stock bottle 28 as in step (8), the Check Point software verifies the DIN/NDC number of the selected pack or stock bottle against the DIN/NDC number as entered into the prescription system, printed in the hardcopy label and approved by the pharmacist to be true as prescribed in the original script. A status message may alert the pharmacist to initiate audio/video communication, optionally as part of the dispensing station equipment, with the technician and oversight the process remotely.

Station 10 has a counting scale 14, or a pill counter, for accurate filling. The quantity of pills to be counted is synchronized electronically between the Check Point software and the counting scale, or pill counter, by step (10). In case of short stock, the software creates a record of owing balances via CPU 12 to be stored in storage mean 18. This minimizes human errors and provides more reliable record keeping. Counting pills directly into vial also avoids cross contamination. The size of the vial is suggested by the Check Point software. This offers safer packaging for patients who are allergic to different medications. The dispensing station enables the pharmacist to supervise, communicate and direct the technician during this process. Further, the system allows the capture of a picture of the prepared vials before being released to the patient.

Thus, Rx script as written to provide medication directions is scanned by receiving means 26, entered into dispensing software 22 and stored in storage means 18. Rx label 30 is generated from dispensing software 22 and has a hard copy vial label upon which patient, prescriber, drug and bill information are printed and. Rx receipt barcode scanned to initiate interface between 22 and CPU 12.

Drug stock bottle 28 is taken from a shelf, stock room or the like to provide the drug to be dispensed. CPU 12 receives information as entered into dispensing software 22, and enables verification of information against written script of 24, stock bottle 28 and controls counting scale 14.

Control of the operation can be achieved using the various software options. In FIG. 4, a snap shot of different status levels 42 are shown on a computer display screen 40 wherein an operator can select one or more status levels, depending on their job responsibilities and/or authorization levels. Access can be controlled by password control, or any other suitable security measure, as required. As such, the operator can focus on their assigned duties.

A brief description of the operational status of various e s shown, by way of example, is as follows:

"Script Pending Entry"—a received prescription by any means, including a written copy handed or fed into the system, a verbal order which is then written down by authorized pharmacy personnel, a received facsimile order, a received copy of an electronically transmitted script, or the like.

"Waiting Validation Approval"—an entered prescription which has been checked by a lower level clerk, and is waiting for pharmacist approval.

"Approved Rx Pending Filling"—pharmacist approved entries, which includes all relevant content which matches the prescribed medication, and with override information where there are mismatches with valid reasons. If not approved, the file is moved to "Rx Pending Re-Entry" status.

"Logged Rx, On Hold"—refers to prescriptions which have not yet been filled.

"Waiting Filling Approval"—refers to prescriptions which have been filled by a technician, after the prescription has been validated by the pharmacist, and which are waiting for the pharmacist to then review and approve the filled contents.

"Approved Rx Pending Release"—After the pharmacist has reviewed the filled vial, and approved the dispensing of the medication, will this status be used. At this point, only billing information is required in order to have the prescription released. Otherwise, the file can be moved to the "Rx Pending Refilling" status.

Of course, other status designations can be included, as required.

As such, the present invention also preferably provides a method as hereinabove described, additionally comprising step-by-step workflow in monitoring and organizing the process of dispensing medication, once the order has been received by any licensed location, to dispense medication until the medication has been released and given to the intended patient.

Thus, it is apparent that there has been provided, in accordance with the present invention, a pharmacy workflow platform, a prescription checking and medicament dispensing station, a network thereof, and methods therewith, which fully satisfies the goals, objects, and advantages set forth hereinbefore. Therefore, having described specific embodiments of the present invention, it will be understood that alternatives, modifications and variations thereof may be suggested to those skilled in the art, and that it is intended that the present specification embrace all such alternatives, modifications and variations as fall within the scope of the appended claims.

Additionally, for clarity and unless otherwise stated, the word "comprise" and variations of the word such as "comprising" and "comprises", when used in the description and claims of the present specification, is not intended to exclude other additives, components, integers or steps. Further, the invention illustratively disclosed herein suitably may be practiced in the absence of any element which is not specifically disclosed herein.

Moreover, the words "substantially" or "essentially", when used with an adjective or adverb is intended to enhance the scope of the particular characteristic; e.g., substantially planar is intended to mean planar, nearly planar and/or exhibiting characteristics associated with a planar element.

Further, use of the terms "he", "him", or "his", is not intended to be specifically directed to persons of the masculine gender, and could easily be read as "she", "her", or "hers", respectively.

Also, while this discussion has addressed prior art known to the inventor, it is not an admission that all art discussed is citable against the present application.

Moreover, although this disclosure has described and illustrated certain preferred embodiments of the invention, it is to be understood that the invention is not restricted to those particular embodiments. Rather, the invention includes all embodiments which are functional or mechanical equivalence of the specific embodiments and features that have been described and illustrated.

The invention claimed is:

1. A pharmacy workflow platform and prescription checking and medicament dispensing station for dispensing a prescribed medicament from a medicament-containing stock bottle, which medicament is prescribed as script data on a prescription, comprising:
   (a) a display screen;
   (b) scanning means for scanning and capturing in electronic format, an image of the prescription containing the script data from said prescription, and for scanning and capturing stock bottle label data from a selected stock bottle from a label on said stock bottle;
   (c) control means for controlling a computing device;
   (d) a computing device controlled by said control means and configured for
      i) receiving and storing said prescription image and stock bottle data in electronic format;

ii) storing data on a plurality of different medicament-containing bottles, in electronic format, and relating said scanned stock bottle data to said stored data on said plurality of different medicament-containing bottles;

iii) receiving script data entered from said control means for said prescription, in electronic format, which entered script data is to be stored on said computing device; and iv) transferring said entered script data, said stock bottle data, and said prescription image, to said display screen to effect display of said stock bottle data, said entered script data, and said prescription image; and (e) a counting scale or pill counter in communication with said computing device, for counting a selected number of dispensed medicaments from said medicament-containing stock bottle, wherein said display screen is used to: (1) visually compare said prescription image with said displayed entered script data to detect and identify any entered script data mistakes, and thereby validate said script data against said prescription; and (2) visually compare said medicament-containing stock bottle data to said prescription image, and thereby validate said dispensed medicament to said prescription.

2. A station as claimed in claim 1 wherein said control means for controlling said computing device is a keyboard, a touch screen, a bar code receiving means and machine readable code means.

3. A station as claimed in claim 1 wherein said scanning means comprises a bar code scanner.

4. A station as claimed in claim 1 further comprising photographic means selected from a camera and web-cam.

5. A station as claimed in claim 1 constituted as an on-site station comprising a bench, table or kiosk.

6. A station as claimed in claim 1 wherein said computing device comprises stored data and is constructed and arranged to compare said script data and said stock bottle label data with said stored data to detect and identify any mistakes.

7. A prescription checking and medicament dispensing network comprising one or more stations as defined in claim 1 in communication with an off-site center.

8. A network as claimed in claim 7 wherein said off-site center is adapted to i) receive said script data and stock bottle label data in electronic format;

ii) receive said prescription and said printed vial label by a photographic means; and iii) to monitor said medicament dispensation.

9. A desired primary source information network comprising a plurality of apparatus as claimed in claim 1.

10. A station as claimed in claim 1 wherein said computing device is a computer.

* * * * *